United States Patent
Glaw et al.

(10) Patent No.: US 12,053,582 B2
(45) Date of Patent: Aug. 6, 2024

(54) VENTILATION CONTROL UNIT AND VENTILATION CONTROL SYSTEM

(71) Applicant: Drägerwerk AG & Co. KGaA, Lübeck (DE)

(72) Inventors: Tobias Glaw, Lübeck (DE); Przemyslaw Gdaniec, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 549 days.

(21) Appl. No.: 17/307,284

(22) Filed: May 4, 2021

(65) Prior Publication Data
US 2021/0338954 A1 Nov. 4, 2021

(30) Foreign Application Priority Data
May 4, 2020 (DE) ...................... 10 2020 002 656.7

(51) Int. Cl.
*A61M 16/00* (2006.01)
*A61M 11/00* (2006.01)
*A61M 16/08* (2006.01)
*A61M 16/14* (2006.01)

(52) U.S. Cl.
CPC ...... *A61M 16/024* (2017.08); *A61M 16/0003* (2014.02); *A61M 16/0891* (2014.02); *A61M 16/147* (2014.02); *A61M 11/00* (2013.01); *A61M 2016/0039* (2013.01); *A61M 2016/0042* (2013.01); *A61M 16/0057* (2013.01);
(Continued)

(58) Field of Classification Search
CPC .......... A61M 16/0051; A61M 16/0057; A61M 16/024; A61M 16/0875; A61M 16/0883; A61M 16/0891; A61M 16/147; A61M 2205/15; A61M 2205/3334; A61M 2016/0039; A61M 11/00
See application file for complete search history.

(56) References Cited

U.S. PATENT DOCUMENTS

| | | |
|---|---|---|
| 7,882,835 B2 | 2/2011 | Eger et al. |
| 9,358,356 B2 | 6/2016 | Hunsicker et al. |
| 10,709,854 B2 | 7/2020 | Jafari et al. |

(Continued)

FOREIGN PATENT DOCUMENTS

| | | |
|---|---|---|
| DE | 60208269 T2 | 8/2006 |
| DE | 102005061439 B3 | 5/2007 |

*Primary Examiner* — Joseph D. Boecker
(74) *Attorney, Agent, or Firm* — McGlew and Tuttle, P.C.

(57) ABSTRACT

A ventilation control unit (100), regulating a gas flow (102) within a ventilation system (105), includes a reception module (120), first and second calculation modules (130, 135) and an output module (140). The reception module has a signal interface (122) receiving inspiratory and expiratory flow signals (125, 127) at regular time intervals. The first calculation module calculates a leak flow (132) based on a difference between the current inspiratory gas flow and the current expiratory gas flow, with an external gas flow source (110) separated from a ventilation circuit of the ventilation system. The second calculation module calculates an external gas flow (136) after connecting the external gas flow source to the ventilation circuit based on the leak flow and the difference between the current inspiratory gas flow and the current expiratory gas flow. The output module outputs an output signal (142), based on the external gas flow.

19 Claims, 4 Drawing Sheets

(52) U.S. Cl.
CPC . *A61M 2205/15* (2013.01); *A61M 2205/3331* (2013.01); *A61M 2205/3334* (2013.01)

(56) References Cited

U.S. PATENT DOCUMENTS

| | | | |
|---|---|---|---|
| 2008/0029092 A1* | 2/2008 | Heesch | A61M 16/01 |
| | | | 128/203.14 |
| 2008/0295837 A1* | 12/2008 | McCormick | A61M 16/0051 |
| | | | 600/529 |
| 2010/0078018 A1* | 4/2010 | Heinonen | A61M 16/01 |
| | | | 128/202.22 |
| 2010/0218767 A1 | 9/2010 | Jafari et al. | |
| 2011/0180063 A1* | 7/2011 | Hunsicker | A61M 16/14 |
| | | | 128/200.14 |

* cited by examiner

VENTILATION CONTROL UNIT AND VENTILATION CONTROL SYSTEM

CROSS REFERENCE TO RELATED APPLICATIONS

This application claims the benefit of priority under 35 U.S.C. § 119 of German Application 10 2020 002 656.7, filed May 4, 2020, the entire contents of which are incorporated herein by reference.

TECHNICAL FIELD

The present invention pertains to a ventilation control unit for regulating a gas flow within a ventilation system with a ventilation circuit and with an external gas flow source connected to the ventilation circuit. The present invention pertains, furthermore, to a ventilation control and to a process for regulating a gas flow within a ventilation system in the presence of an external gas flow source.

TECHNICAL BACKGROUND

An inspiratory gas flow, which is at least partially inhaled by a person, is provided for the person in question by a connected ventilation system during the ventilation of the person. The part of the fed gas that is guided into the mouth of the person is also called patient gas flow. The air exhaled by the person contributes to an expiratory gas flow of the ventilation system, which is moved away from the person and is typically subjected to further processing, for example, by a $CO_2$ absorber or the like.

It is known that the gas flows are monitored within a ventilation system in order to ensure a necessary ventilation of a person connected to the ventilation system. In particular, it is ensured by a monitoring of the expiratory gas flow that a leak within the gas guiding system of the ventilation system is detected if it leads to a substantial reduction of the quantity of gas made available to the person.

It is known especially from U.S. Pat. No. 9,358,356 B2 that an external gas flow of an external gas flow source, e.g., of an atomizer, is monitored and the inspiratory gas flow is reduced if the additional external gas flow causes an excessively large gas flow to the patient.

SUMMARY

An object of the present invention is to provide an improved regulation of the gas flow within a ventilation system, especially an improved monitoring of the underlying gas flows.

To accomplish this object, a ventilation control unit for regulating a gas flow within a ventilation system with a ventilation circuit and with an external gas flow source connected to the ventilation circuit is proposed according to a first aspect of the present invention to regulate a gas flow within a ventilation system. The ventilation control unit according to the present invention has a reception module, a first calculation module, a second calculation module and an output module.

The reception module has a signal interface, which is configured repeatedly to receive an inspiratory flow signal and an expiratory flow signal, especially to receive it at regular time intervals, wherein the inspiratory flow signal indicates a current inspiratory gas flow and the expiratory flow signal indicates a current expiratory gas flow.

The first calculation module is configured to calculate a leak flow on the basis of a difference between the current inspiratory gas flow and the current expiratory gas flow, while the external gas flow source is separated from the ventilation circuit of the ventilation system. The first calculation module is configured, furthermore, to output a leak signal, which indicates the calculated leak flow.

The second calculation module is configured to receive the leak signal and to calculate an external gas flow after reception of the leak signal and after connection of the external gas flow source to the ventilation circuit of the ventilation system on the basis of the calculated leak flow and of the difference between the current inspiratory gas flow and the current expiratory gas flow.

The output module is configured to output an output signal, which is based on the calculated external gas flow. In particular, the output module is configured to make the calculated external gas flow available through the output signal for the further processing, especially for a regulation of the inspiratory gas flow.

It was found within the framework of the present invention that the external gas flow is typically applied as an essentially constant external gas flow or it is applied with a regularly recurring amplitude variation, whereas the leak flow may change over time. It was proposed therefore according to the present invention to calculate a leak flow, especially a temporary leak flow, in a first step without external gas flow source, in order to calculate the external gas flow of the external gas flow source, which is to be connected now, taking this leak flow into account. All essential gas flows within the ventilation system can be detected quantitatively in this manner, which makes possible an especially precise calculation of the patient gas flow fed to the patient.

The present invention advantageously makes it possible to determine a current leak flow and the external gas flow of an external gas flow source. This is especially advantageous for such external gas flow sources, which are not controlled quantitatively via the ventilation system, so that their external gas flow may not be readily known to the ventilation system. A possible example of such an external gas flow source is an atomizer, which feeds a drug to the patient via the external gas flow.

The two-step determination being proposed for determining the external gas flow can be carried out especially advantageously in a clinical setting, because the ventilation system is typically already operating before the external gas flow source is introduced into the ventilation system. The first calculation module can therefore already calculate the leak flow before the external gas flow source is introduced into the ventilation system and the second calculation module assumes the calculation of the external gas flow. It is consequently unnecessary to shut the external gas flow source off and on separately for the regulation of the gas flow, especially of the inspiratory gas flow, according to the present invention.

The reception of the inspiratory flow signal and of the expiratory flow signal at repeated time intervals, especially at regular time intervals, ensures that a change in the ability of a connected ventilator to function and/or an error within the ventilation circuit, such as an excessively large leak flow, can be detected in a short time.

If the external gas flow has been calculated and thereby measured, the external gas flow source can then also be separated again from the ventilation circuit and connected, without a repeated measurement of the external gas flow being necessary, because the external gas flow is typically constant over time for the same source.

The calculation of the external gas flow may also comprise according to the present invention the calculation of an external gas flow curve, for example, in case of the use of a regularly pulsed external gas flow source. The external gas flow curve measured in this manner can be processed further corresponding to the embodiments according to the present invention, which will be explained below, in exactly the same manner as a calculated constant external gas flow. An external gas flow will always be defined below in this sense as a constant value of an external gas flow or as a recurring external gas flow curve. For the determination of the external gas flow curve, the expiratory gas flow can preferably be outputted at short time intervals such that a curve of the external gas flow, which is resolved over time, can be calculated according to the present invention. Details of this calculation are explained within the framework of the description of the figures.

The calculation based on the difference of two gas flows may mean according to the present invention a calculation to determine a volume difference. Thus, a gas flow is a gas volume per unit of time, and the adding up of consecutive differences of gas flows therefore yields a volume difference for these gas flows.

A ventilation circuit in the sense of the present invention may be an open or closed ventilation circuit. In particular, it may be a closed ventilation circuit, in which the gas exhaled by the patient is returned to a ventilator, or it may be an open ventilation circuit, in which gas exhaled by the patient escapes from the system.

The expiratory gas flow and the inspiratory gas flow are current in the sense of the present invention if they were received within a short past time range by the corresponding inspiratory flow signal and by the corresponding expiratory flow signal. The short past time range is a past time range that is relevant for the analysis of the ventilation system, e.g., a time range of less than 10 minutes, especially a time range of less than 5 minutes, especially preferably a time range of less than 2 minutes. Thus, the calculation according to the present invention by the second calculation may be based on the same current inspiratory gas flow that was already used for the first calculation module for the calculation of the leak flow. The inspiratory gas flow through the ventilator does not change due to the connection of the external gas flow source to the ventilation circuit, so that the current inspiratory gas flow within the first calculation module is also current after the connection to the external gas flow source in the sense of the present invention.

The output signal indicates according to the present invention information that is based on the calculated external gas flow. This may be the calculated external gas flow itself or a variable derived from the calculated external gas flow.

The modules of the ventilation control unit according to the present invention may be configured as modules located at spaced locations from one another or in a common device, especially in a common housing. At least two of the modules are preferably configured on a common processor. The modules are processing units separated at least at the software level.

The reception module may be composed of a plurality of reception submodules separated in space, which are configured to receive the exhalation signal and/or the inhalation signal independently from one another. In particular, a reception submodule may be arranged in the vicinity in space of additional modules of the ventilation control unit, while another reception submodule is located at a spaced location from additional modules of the ventilation control unit.

The inspiratory gas flow is, in the sense of the present invention, the gas flow that is provided by the ventilator. Thus, both the inspiratory gas flow and the external gas flow are added for a patient connected to the ventilation circuit, whereas the expiratory gas flow and the leak flow are directed away from the patient.

According to the present invention, the ventilation circuit with the external gas flow source connected to the ventilation circuit is not a part of the ventilation control unit, but of the ventilation system. In one embodiment, the external gas flow source or at least a part of the external gas flow source, for example, a control module of the external gas flow source, is a part of the ventilation control unit according to the present invention.

The external gas flow source is separated in the sense of the present invention from the ventilation circuit if no gas flow is possible from the external gas flow source into the ventilation circuit. Such a separation can consequently be brought about, for example, by actually removing the external gas flow source or by closing a corresponding flow duct, for example, by shutting off the external gas flow source.

The external gas flow caused by the external gas flow source may be a negative gas flow under certain circumstances. Thus, the external gas flow source may be configured, for example, to move an aspirating gas flow out of the ventilation circuit for taking a gas sample.

Preferred embodiments of the ventilation control unit according to the present invention will be described below.

In an especially preferred embodiment, the ventilation control unit has, furthermore, a regulating module, which is configured to receive the output signal and to trigger a regulation of the inspiratory gas flow on the basis of the calculated external gas flow. The gas flow fed to the patient can advantageously be regulated in this embodiment as a function of the calculated external gas flow, so that, for example, a maximum overall gas flow to be provided will not be exceeded, for example, in a variant of this embodiment. The inspiratory gas flow provided by the ventilation is preferably reduced by the volume flow that is added to the ventilation circuit due to the external gas flow via the external gas flow source.

The external gas flow source is preferably an atomizer. The ventilation control unit according to the present invention is especially advantageous in the case in which the external gas flow source does not comprise any gas flow sensor, which measures the external gas flow, so that this external gas flow is to be calculated according to the present invention within the ventilation control unit according to the present invention. Such an atomizer provided as an external gas flow source typically feeds a drug into the ventilation circuit and hence also into the gas inhaled by the patient via the external gas flow.

In an especially advantageous embodiment, the leak flow and/or the external gas flow are determined on the basis of a plurality of inspiratory and expiratory gas flows of a corresponding plurality of breaths of a person connected to a ventilation system. Taking a plurality of breaths into consideration makes it advantageously possible in a variant of this embodiment to form a mean value, by which temporary atypical changes in the gas flows are not taken into consideration in the calculation of the leak flow or of the external gas flow so strongly as is a long-term change in these gas flows. In particular, a basic trend of the inspiratory and expiratory gas flow rather than a short-term change is taken into consideration thereby in the calculation of the gas flow and/or of the leak flow. In an alternative or additional variant of this embodiment, the fact that a plurality of breaths are taken into consideration makes possible the application of a low-pass filter in order not to take temporary atypical changes of the gas flows so strongly into consideration. Such a low-pass filter may be, for example, a Bessel filter, a PT1 unit or a Chebyshev filter. As an alternative or in addition, the low-pass filter can filter out the periodic changes on the basis of the breathing process in order thus to analyze a constant predefined inspiratory and/or expiratory gas flow.

The ventilation control unit can preferably detect a one-time atypical ventilation event, for example, a cough of the patient being ventilated, especially on the basis of the corresponding atypical gas flow or pressure curve, and exclude a breath with such an atypical ventilation event from the averaging over a plurality of breaths and/or from the further analysis. As a result, an especially precise determination of a leak flow and/or external gas flow is possible, because undesired interfering effects, such as a cough or sneezing, are filtered out.

In a preferred embodiment, the ventilation control unit according to the present invention is configured to receive the calculated external gas flow and to calculate the leak flow on the basis of the calculated external gas flow and on the basis of the difference between the current inspiratory gas flow and the current expiratory gas flow. The leak flow is calculated for an additional time in this embodiment. In a preferred variant, the leak flow is determined again at regular intervals after the calculation of the external gas flow. As a result, a change in the leak flow can be detected in a short time in an especially advantageous manner. This is advantageous because the leak flow is susceptible to short-term changes due to a short-term change in the ventilation circuit, for example, due to an additional leak flow. The calculated external gas flow is typically maintained at a constant level over a predefined treatment period, so that this does not need to be determined repeatedly and can be used for the future determination of the leak flow.

In an especially preferred embodiment, the ventilation control unit has, furthermore, an additional calculation module, which is configured to calculate a patient gas flow fed to the patient on the basis of the calculated external gas flow, on the basis of the calculated leak flow and on the basis of the difference between the current inspiratory gas flow and the current expiratory gas flow. The output signal outputted by the output module preferably indicates here the patient gas flow. The determination of the patient gas flow advantageously makes it possible to detect the quantity of the gas fed to the patient. The fact that all the currently occurring gas flows through the ventilation control unit according to the present invention, which are necessary for balancing the gas flows, are known, is advantageously utilized in this embodiment. Additional effects, for example, the volume change in the tube system on the basis of pressure or temperature changes, can be taken into consideration by means of known calculation processes, for example, the calculation of the known hose compliance flow. Such effects should be taken into consideration in the sense of this invention within the inspiratory gas flow and/or within the expiratory gas flow. The patient gas flow is a variable relevant for the clinical treatment of a patient. In particular, it is advantageous to regulate the inspiratory gas flow, especially to regulate it by a regulating module of the ventilation control unit, depending on the determined patient gas flow. It is possible to ensure hereby the provision of a predefined tidal volume of the ventilation by the ventilation system.

According to a second aspect of the present invention, a ventilation system with a ventilation circuit and with an external gas flow source connected to the ventilation circuit, which gas flow source comprises a ventilation control unit according to at least one of the above embodiments, is proposed to accomplish the above-mentioned object.

The ventilation system according to the present invention has all the advantages that the ventilation control unit according to the present invention has. Furthermore, it is advantageous in the ventilation system according to the present invention that the ventilation control unit can be coordinated with the other components of the ventilation system.

The ventilation system according to the present invention preferably comprises at least one first measuring unit, which measures the inspiratory gas flow and outputs a corresponding inspiratory flow signal, and at least one second measuring unit, which measures the expiratory gas flow and outputs a corresponding expiratory flow signal. The first and second measuring units are connected to the reception module of the ventilation control unit in a cable-based or wireless manner.

In a preferred embodiment, the ventilation system has, furthermore, a control module for the external gas flow source, wherein the control module is configured to keep the external gas flow source separate from the ventilation circuit prior to the reception of the leak signal provided by the first calculation module and to trigger a connection of the external gas flow source to the ventilation circuit at the time of receiving the leak signal. It is ensured in this preferred embodiment that corresponding to the procedure according to the present invention, the external gas flow source is separate from the ventilation circuit of the ventilation system during the calculation of the leak flow by the first calculation module and that the external gas flow source is in connection with the ventilation circuit of the ventilation system during the calculation of the external gas flow. Manual errors during the handling of the ventilation system according to the present invention are avoided by such an automated control of the connection of the external gas flow source to the ventilation system. It is thus avoided, for example, that the external gas flow is calculated without the external gas flow source being connected to the ventilation circuit and/or that the leak flow is calculated for the first time while the external gas flow source is connected to the ventilation circuit. The calculation according to the present invention of the external gas flow is consequently supported especially reliably by the ventilation system according to this embodiment.

In another embodiment, the ventilation system has a pressure analysis module, which is configured to infer the performed connection of the external gas flow source on the basis of the pressure present within the ventilation circuit at at least one position. This conclusion may be based, for example, on a percentage of the pressure present within the tube system, which percentage is independent from the breathing rhythm. As an alternative or in addition, the pressure analysis module may be configured to infer an atypical current event, for example, a cough or a sneezing of the person being ventilated on the basis of a measured pressure curve over time and then to correspondingly influence the further processing of currently obtained data, especially to prevent it during the presence of an atypical current event.

It is possible, moreover, to exclude additional breaths from the calculation of the leak flow when it is foreseeable that the quality of the calculation of the leak flow is currently compromised. For example, the quality may be compromised by a change in at least one ventilation setting, e.g., the end-expiratory ventilation pressure (PEEP), the ventilation mode, the tidal volume and/or a predefined time characteristic of the ventilation.

The calculation of the external gas flow is based, in principle, on the assumption that the leak proper, i.e., for example, the unintended leak at the patient port, has remained as constant as possible between the calculation processes carried out by the first and second calculation modules. Differences in the difference of inspiratory and expiratory gas flow should only be caused by the inclusion of the external gas flow of the external gas flow source. The leak flow between or during the two calculation processes of the two calculation modules is preferably monitored therefore in order to detect a change in the leak flow. In case of excessively great changes in the leak flow within the respective calculation modules, a warning can be outputted to the user, or he may be prompted to repeat the measurement and/or calculation in question via a user interface. The probability of an external gas flow determined with a major error can be reduced hereby.

According to a third aspect of the present invention, a process for regulating a gas flow within a ventilation system in the presence of an external gas flow source is proposed to accomplish the above-mentioned object. The process according to the present invention has the following steps:
  reception of a first inhalation signal, which indicates a current inspiratory gas flow, and of a first exhalation signal, which indicates a current expiratory gas flow;
  calculation of a leak flow based on a difference between the current inspiratory gas flow and the current expiratory gas flow, while the external gas flow source is separated from a ventilation circuit of the ventilation system;
  outputting of a leak signal, which indicates the determined leak flow;
  reception of a second exhalation signal, which indicates a current expiratory gas flow after the calculation of the leak flow;
  calculation of an external gas flow after reception of the leak signal and after connection of the external gas flow source to the ventilation circuit of the ventilation system on the basis of the calculated leak flow and on the basis of the difference between the current inspiratory gas flow and the current expiratory gas flow; and
  outputting of an output signal, which is based on the calculated external gas flow.

The process according to the present invention has a two-step maneuver for measuring the external gas flow, in which the leak flow is determined at first in order to then determine the external gas flow on the basis of the leak flow.

The process according to the present invention has the same advantages as the ventilation control unit according to the present invention according to the first aspect of the present invention. The process according to the present invention makes possible, in particular, a determination of the leak flow independently from the external gas flow and a subsequent, especially precise determination of the external gas flow. Thus, the process according to the present invention ensures that the relevant gas flows within the ventilation circuit are calculated reliably and can be taken into consideration for further processing, for example, for determining the patient gas flow.

In an especially preferred embodiment, a last step comprises a regulation of the inspiratory gas flow on the basis of the calculated external gas flow. A total gas volume made available for the patient per breath can be regulated hereby. In particular, the inspiratory gas flow can be reduced by the quantity of gas volume fed externally per unit of time.

In another, especially advantageous embodiment, the inspiratory gas flow is regulated, furthermore, on the basis of the calculated leak flow. The inspiratory gas flow can be regulated especially precisely in this embodiment, which is an additional or alternative embodiment to the previous embodiment, in such a way that a predefined gas flow is present at a predefined point of the ventilation circuit, for example, at the patient, during the operation of the corresponding ventilation system, especially independently from a possible leak or of an external gas flow source.

In another embodiment, the process has, furthermore, a reception of a second inhalation signal, which indicates a current inspiratory gas flow after the calculation of the leak flow, especially after the output of the leak signal. The last measured inspiratory gas flow is used for the calculation of the external gas flow in this preferred embodiment. Since the inspiratory gas flow may change over time for various reasons, the taking into account of the last measured inspiratory gas flow, especially of an inspiratory gas flow measured once again after the calculation of the leak flow, leads to an especially current inspiratory gas flow for the calculation of the external gas flow. As a result, the calculated value for the external gas flow can be especially accurate.

In a preferred embodiment, the process according to the present invention has, furthermore, a repeated calculation of the leak flow on the basis of the calculated external gas flow and on the basis of the difference between the current inspiratory gas flow and the current expiratory gas flow. The leak flow continues to be determined continuously after the determination according to the present invention of the external gas flow in this preferred embodiment. This is advantageous especially because a leak flow typically develops in an unforeseen manner, so that its detection without undue delay by the medical staff or by the ventilation system is advantageous. In particular, countermeasures, such as closure of a leak or an increase in the inspiratory gas flow, can be initiated without undue delay hereby.

The present invention shall now be explained in more detail on the basis of advantageous exemplary embodiments shown schematically in the figures.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
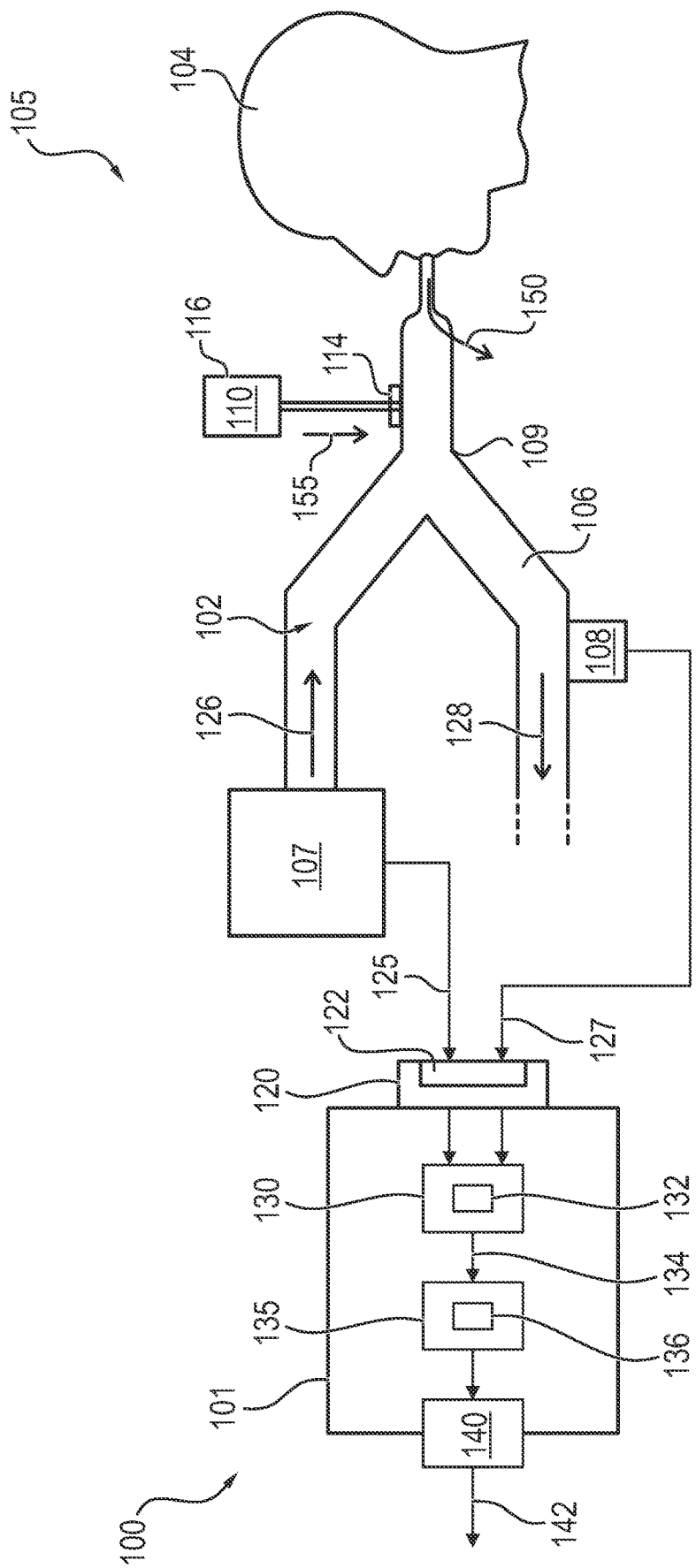
FIG. 1 is a schematic view of a first exemplary embodiment of a ventilation control unit according to a first aspect of the present invention within a ventilation system according to a second aspect of the present invention.

Referring to the drawings, FIG. 1 shows a schematic view of a first exemplary embodiment of a ventilation control unit 100 according to a first aspect of the present invention within a ventilation system 105 according to a second aspect of the present invention.

The ventilation control unit 100 is configured to regulate a gas flow 102 within the ventilation system 105 with a ventilation circuit 106 and with an external gas flow source 110 connected to the ventilation circuit 106. The ventilation system 105 has here, furthermore, a ventilator 107 providing an inspiratory gas flow 126. Finally, the ventilation system 105 also has an expiratory gas flow sensor 108, which measures the expiratory gas flow 128. The ventilation circuit 106 passes over a Y-piece 109 to a patient 104 to be supplied with the ventilation system 105. The further course of the gas flow 102 on the exhalation side of the ventilation circuit 106 is not shown in detail and is not relevant for accomplishing the object according to the present invention. For example, gas exhaled by the patient 104 in the case of anesthesia is returned via a $CO_2$ absorber to the inspiratory gas flow 126.

The ventilation control unit 100 comprises a reception module 120, a first calculation module 130, a second calculation module 135 and an output module 140.

The reception module 120 has a signal interface 122, which is configured to receive an inspiratory flow signal 125 and an expiratory flow signal 127 at regular time intervals, wherein the inspiratory flow signal 125 indicates a current inspiratory gas flow 126 and the expiratory flow signal 127 indicates a current expiratory gas flow 128. The regular time intervals are preferably time intervals shorter than 10 sec, especially shorter than 5 sec, preferably shorter than 2 sec. In a preferred variant, the inspiratory flow signal 125 is provided by the ventilator 107 essentially continuously and is received through the signal interface 122, wherein the ventilator 107 comprises an inspiratory flow sensor, not shown, which measures the current inspiratory gas flow 126. As an alternative or in addition, the expiratory flow signal 127 is provided essentially continuously by the expiratory gas flow sensor 108 in this variant. The reception according to the present invention at regular time intervals may thus also comprise short, technically related time intervals shorter than 0.5 sec. In a preferred variant of the exemplary embodiment shown, the current inspiratory gas flow 126 and the current expiratory gas flow 128 are analyzed by an analysis of the corresponding inspiratory flow signal 125 or of the expiratory flow signal 127 at certain time intervals only.

The first calculation module 130 is configured to receive corresponding information concerning the current inspiratory gas flow 126 and the current expiratory gas flow 128 and to calculate a leak flow 132 on the basis of this. This calculation is based on a difference between a current inspiratory gas flow 126 and a current expiratory gas flow 128. In order for the calculated leak flow 132 to correspond essentially to the actually occurring leak flow 150, which is represented here as an example at a mouthpiece to the patient 104, the leak flow 132 is calculated only when the external gas flow source 110 with its unknown external gas flow 155 is separated from the ventilation circuit 106 of the ventilation system 105. Finally, the first calculation module 130 is configured, furthermore, to output a leak signal 134, which indicates the calculated leak flow 132.

This leak signal 134 is received together with information concerning the current inspiratory gas flow 126 and together with the current expiratory gas flow 128 by the second calculation module 135, wherein the two flow signals 125 and 127 are not shown as arriving at the second calculation module 135 for clarity's sake. The second calculation module 135 is configured here to determine the external gas flow 136 on the basis of the calculated leak flow 132 and on the basis of the difference between the current inspiratory gas flow 126 and the current expiratory gas flow 128 after connection of the external gas flow source 110 to the ventilation circuit 106 and after reception of the leak signal 134. Due to the calculated leak flow 132 being taken into consideration in the calculation of the external gas flow 136, the calculated external gas flow 136 preferably corresponds extensively to the external gas flow 155 actually present through the external gas flow source 110. The actually present external gas flow 155 is fed in the area of the Y-piece 109 in the ventilation system 105 being shown.

The output module 140 is configured to output an output signal 142, which is based on the calculated external gas flow 136. The output signal 142 indicates the calculated external gas flow 136 in the exemplary embodiment being shown.

As is shown in FIG. 1, a manual connection and separation of the external gas flow source 110 is necessary in the exemplary embodiment shown corresponding to the manner of functioning of the ventilation control unit 100. Thus, the external gas flow source 110 is not connected at the ventilation circuit 106 during the calculation of the leak flow 132 by the first calculation module 130. After connection of the external gas flow source 110 via an external gas port 114 to the Y-piece 109, the calculation of the external gas flow 155 can be carried out by the second calculation module 135. A connection and separation of the external gas flow source is carried out in an automated manner, especially in an automated manner via a corresponding control module, in other exemplary embodiments. The external gas flow source may be arranged according to the present invention permanently at the ventilation circuit and activated or deactivated, especially activated or deactivated in an automated manner. This is comprised by the separation and connection according to the present invention of the external gas flow source in the corresponding exemplary embodiment. In one exemplary embodiment, not shown, the external gas flow source is arranged directly behind the ventilator and in front of the Y-piece or it is arranged in another area of the ventilation circuit between the ventilator and the patient.

All modules of the ventilation control unit 100 according to the present invention are arranged in the exemplary embodiment shown in a common device, especially in a common housing 101. In other exemplary embodiments, at least one module is not arranged in a common housing with the other modules.

The processing by the modules according to the present invention of the ventilation control unit 100, especially the processing by the first calculation module 130 and by the second calculation module 135, may be carried out at least partially by a common processor. The modules are processing units separated at least at the software level.

The external gas flow source 110 is an atomizer 116 in the exemplary embodiment being shown. In one exemplary embodiment, not shown, the external gas flow source is a tracheal gas insufflator.

The calculation of the leak flow 132 and of the external gas flow 136 is carried out by balancing the respective gas flows currently present in the ventilation circuit 106. The leak flow 132 is calculated during a first calculation maneuver by the first calculation module 130, and the external gas flow 136 is calculated during a second calculation maneuver by the second calculation module 135.

The first calculation maneuver by the first calculation module 130 is based on the fact that the leak flow $F_L$ is obtained directly from the difference between the inspiratory gas flow $F_I$ and the expiratory gas flow $F_E$, because, aside from the leak flow, the inspiratory gas flow and the expiratory gas flow, no other gas flows are present in the ventilation circuit. In a preferred variant of this exemplary embodiment, the leak flow $F_L$ is determined on the basis of a plurality of inspiratory and expiratory gas flows of a corresponding plurality of breaths of the patient 104. This calculation is preferably carried out by forming the difference of the mean values of the inspiratory gas flow and the expiratory gas flow. In an alternative or additional variant, a processing of the plurality of inspiratory and expiratory gas flows or of the plurality of differences of inspiratory and expiratory gas flows by means of a filter function, especially by means of a low-pass filter, is employed. Such a low-pass filter may be, for example, a Bessel filter, a PT1 unit or a Chebyshev filter. Such a low-pass filter ensures that a temporary disturbance in the regular breathing rhythm is not taken into consideration or is hardly taken into consideration in the calculation of the leak flow. Thus, such a temporary disturbance has a lower frequency than the regular breathing rhythm, so that it can be filtered out by means of such a low-pass filter. The signal left after this filtering is periodic based on the breathing rhythm and can be analyzed in view to the respective known gas flow concerning the inspiratory and expiratory gas volumes per breath. The filtering by the low-pass filter may be provided, in addition or as an alternative, such that the respiration rate is filtered out, so that, for example, the inspiratory and/or expiratory gas flow provided can be read as a constant signal component as a result of the low-pass filtering. The use of mean values of a plurality of inspiratory gas flows and of a plurality of expiratory gas flows and the use of filtered values may be combined with one another.

The second calculation maneuver by the second calculation module 135 is based on the fact that the external gas flow $F_{EX}$ is fed to the ventilation circuit 106 due to the connection to the external gas flow source 110. Taking into consideration the assumption that the patient gas flow is, on average, zero, since the gas flowing into the patient also flows again out of the patient, a balancing of the occurring gas flows thus yields the following equation:

$$0 = F_I - F_E - F_L + F_{EX}.$$

This equation is an equation averaged over one or more inhalation and exhalation phase/phases. This equation obviously corresponds to a corresponding equation for the respective gas flow volumes present. The inspiratory gas flow $F_I$ and the external gas flow $F_{EX}$ are fed to the patient and they therefore have a plus sign and the expiratory gas flow $F_E$ and the leak flow $F_L$ lead away from the patient and they therefore have a minus sign. The possible determination equation $F_{EX} = -F_I + F_E + F_L$ is thus obtained directly for the determination of the external gas flow. According to the present invention, the second calculation module 135 uses this determination equation directly for a respective pair of current respiratory gas flow and current expiratory gas flow or for a plurality of inspiratory and expiratory gas flows from a corresponding plurality of breaths of the patient. The leak during the two calculation maneuvers is preferably assumed here to be constant, so that the leak flow determined in the first calculation module or the leak volume determined therefrom in the first calculation step is used for this calculation.

As an alternative or in addition, a leak guideline value is calculated corresponding to a leak model on the basis of a plurality of inspiratory and expiratory gas flows of a corresponding plurality of breaths and the leak flow is determined from this. For example, the leak guideline value is based on a value for the difference between the current inspiratory gas flow and the current expiratory gas flow, which value is averaged over a certain time period. The leak guideline value is assumed to be constant over a certain time period, especially over the two calculation maneuvers. The leak flow is preferably a pressure-dependent leak flow and/or the leak guideline value is a pressure-dependent leak guideline value.

As an alternative or in addition, another leak model can be used to calculate the leak flow. The leak model can estimate the current leak flow on the basis of a current pressure at the patient port (Paw). An example of this would be an exponential leak model, which estimates the leak flow $F_L$ with the following equation:

$$F_L = G\alpha^*(\text{Paw})^\wedge\alpha$$

Here, $G\alpha$ and $\alpha$ are values to be estimated by the leak algorithm according to the leak model. This process is known from DE 10 2005 061 439 B3 and may be combined with additional parameters to be measured (corresponding U.S. Pat. No. 7,882,835 (B2) is incorporated herein by reference in it entirety).

The last currently received values for the current inspiratory gas flow and for the current expiratory gas flow are used in the calculation according to the present invention of the leak flow and/or external gas flow. However, only the last currently received value for the expiratory gas flow is used, as an alternative, in one exemplary embodiment, not shown, whereas the inspiratory gas flow is an inspiratory gas flow set or predefined within a treatment process. This inspiratory gas flow is provided currently according to the present invention at least for the first calculation maneuver by the first calculation module. The exemplary embodiment configured in this manner makes possible the manner of functioning according to the present invention of the ventilation control unit due to the inspiratory gas flow being essentially able to be maintained at a constant value for a ventilator that is able to function. Consequently, a regular determination of the inspiratory gas flow is not necessary. The inspiratory gas flow can be set according to the present invention and it can be outputted to the ventilation control unit via the inhalation signal. An inspiratory gas flow set in this manner is also a current inspiratory gas flow in the sense of the present invention, because this inspiratory gas flow can be assumed to be currently present.

The signals within the ventilation control unit according to the present invention can be transmitted in a cable-based or wireless manner. The respective signal transmission takes place in the exemplary embodiment being shown by a cable-based communication of the respective modules with one another, wherein the first calculation module and the second calculation module are embodied by a common processor.

The sensor for measuring the inspiratory or expiratory gas flow is preferably a commercially available flow sensor. This may be based, for example, on an ultrasound method, on a differential pressure method or on a magnetic inductive measurement.

Figure 2:
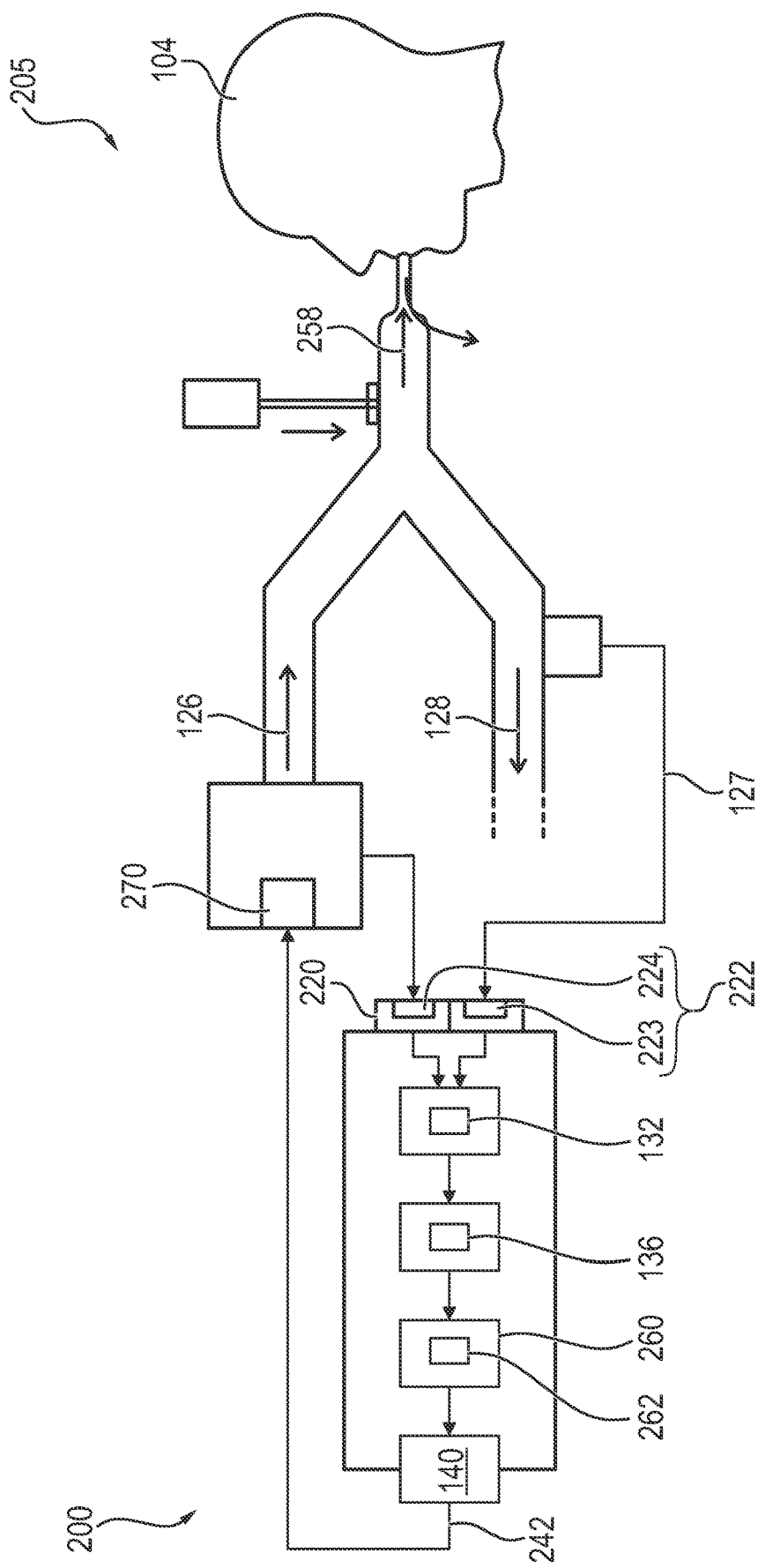
FIG. 2 is a schematic view of a second exemplary embodiment of the ventilation control unit according to the first aspect of the present invention within the ventilation system according to the second aspect of the present invention.

FIG. 2 shows a schematic view of a second exemplary embodiment of the ventilation control unit 200 in accordance with the first aspect of the present invention within the ventilation system 205 according to the second aspect of the present invention.

The ventilation control unit 200 differs from the ventilation control unit 100 shown in FIG. 1 in that the reception module 220 has a signal interface 222, which comprises two separate components 223, 224 in order to receive the inspiratory flow signal 125 and the expiratory flow signal 127.

Further, the ventilation control unit 200 is distinguished by the fact that it comprises an additional calculation module 260, which is configured to calculate a patient gas flow 258 fed to the patient on the basis of the calculated leak flow 132 and the calculated external flow 136 as well as from the difference between the current inspiratory gas flow 126 and the current expiratory gas flow 128. The patient gas flow 258 fed to the patient comprises a gas volume, which corresponds essentially to the so-called tidal volume during the ventilation of the patient 104. The calculated patient gas flow 262 corresponds essentially to the patient gas flow 258 actually fed to the patient on the basis of the reliable calculation of the leak flow 232 and of the external gas flow 236. The calculation of the fed patient gas flow $F_L$ is obtained on the basis of the already explained balancing of the existing gas flows within the breathing process as follows:

$$F_P = F_I - F_E - F_L + F_{EX}$$

Contrary to the balance equation already described, the variables used in this equation are not values averaged over time, so that it cannot be assumed here that the patient gas flow is zero, because the patient gas flow is analyzed rather than averaged during the ventilation process. Consequently, at least the current expiratory gas flow 128 is analyzed for the calculation of the fed patient gas flow by the additional calculation module 260. The patient gas flow 258 actually fed to the patient is an important variable for regulating the ventilator 107. For example, the patient gas flow can thus be fed such that a predefined tidal volume of the ventilation is reached.

The output signal 242 of the output module 140 is outputted directly to the ventilator 107 and it indicates the calculated patient gas flow 262. A regulating module 270 is configured in the ventilator 107 to receive the output signal 242 and to carry out a regulation of the inspiratory gas flow 126 on the basis of the calculated patient gas flow 262. The calculated patient gas flow is now compared with a predefined desired patient gas flow corresponding to the predefined tidal volume of the ventilation and the inspiratory gas flow 126 provided is regulated correspondingly.

In one exemplary embodiment, not shown, the regulating module is arranged in a common housing with the additional modules of the ventilation control unit. The regulating module is preferably a part of the ventilation control unit according to the present invention.

Figure 3:
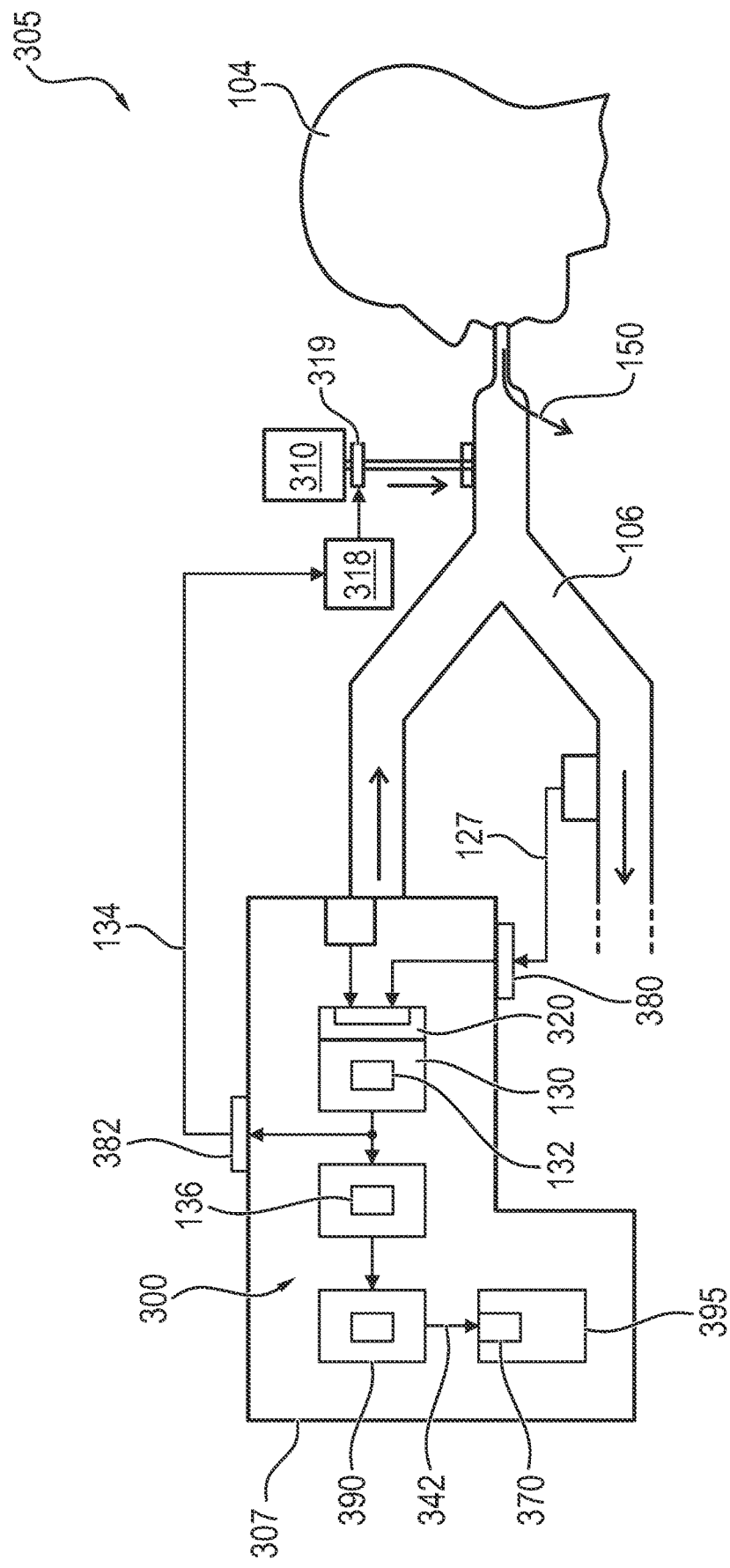
FIG. 3 is a schematic view of a third exemplary embodiment of the ventilation control unit according to the first aspect of the present invention within the ventilation system according to the second aspect of the present invention.

FIG. 3 shows a schematic view of a third exemplary embodiment of the ventilation control unit 300 according to the first aspect of the present invention within the ventilation system 305 according to the second aspect of the present invention.

The ventilation control unit 300 differs from the ventilation control unit 100 shown in FIG. 1, among other things, in that it is arranged within the ventilator 307. The signal interface of the reception module 320 is therefore an internal signal interface within the ventilator 307. The ventilator 307 has a first external interface 380 for receiving the expiration flow signal 127. Furthermore, the ventilation control unit 300 and the ventilation system 305 enclosing same are distinguished in that the leak signal 134 is sent via a second external interface 382 to a control module 318 of the external gas flow source 310 or is polled from this control module 318. The control module 318 is a part of the external gas flow source 310 in the exemplary embodiment shown. In one exemplary embodiment, not shown, the control module 318 is a separate module, which communicates with the external gas flow source 310 via a correspondingly provided communication channel. The control module 318 is configured to trigger a connection of the external gas flow source 310 to the ventilation circuit 106 by receiving the leak signal. This is brought about by opening an opening device 319, especially an opening valve.

In one exemplary embodiment, not shown, a user interface is provided, which is configured to receive a user input, which indicates whether the external gas flow source is connected or detached, i.e., for example, whether the external gas flow source is activated or deactivated or whether a corresponding valve is opened or closed for the hydrodynamic connection of the external gas flow source to the ventilation circuit. The ventilation control unit can thus learn something about the state of the external gas flow source without an electrical or mechanical connection being necessary for sending a corresponding signal. The user interface may comprise, for example, a touch display, a keyboard, a setting wheel, a switch and/or a touchpad.

Furthermore, the ventilation control unit 300 is distinguished in that the calculated external gas flow 136 is used together with the current expiratory gas flow and with the current inspiratory gas flow within an additional module 390 to calculate the current leak flow 150. It is assumed in this case that the external gas flow is constant over time and this external gas flow can consequently be assumed to be a constant value, as was described above, within the balance of the occurring gas flows. As a result, the valve originally calculated for the leak flow 132 by this first calculation module 130 is discarded and determined anew and/or averaged over time. The long-lasting analysis of the current leak flow advantageously makes it possible to rapidly detect a suddenly occurring leak and hence a corresponding readjustment of the ventilator 307 for providing the predefined patient flow corresponding to the predefined tidal volume for the ventilation of the patient 104.

The output signal 342 is sent corresponding to the structure of the ventilation system 305 via an internal, cable-based connection to the regulating module 370 of the ventilator 307. The regulating module 370 forms a part of a processing unit 395 of the ventilator 307.

In an advantageous exemplary embodiment, not shown, the control module of the external gas source is connected to the ventilation control unit such that a calculation of the external gas flow through the second calculation module is triggered by the connection of the external gas source to the ventilation circuit of the ventilation system.

Figure 4:
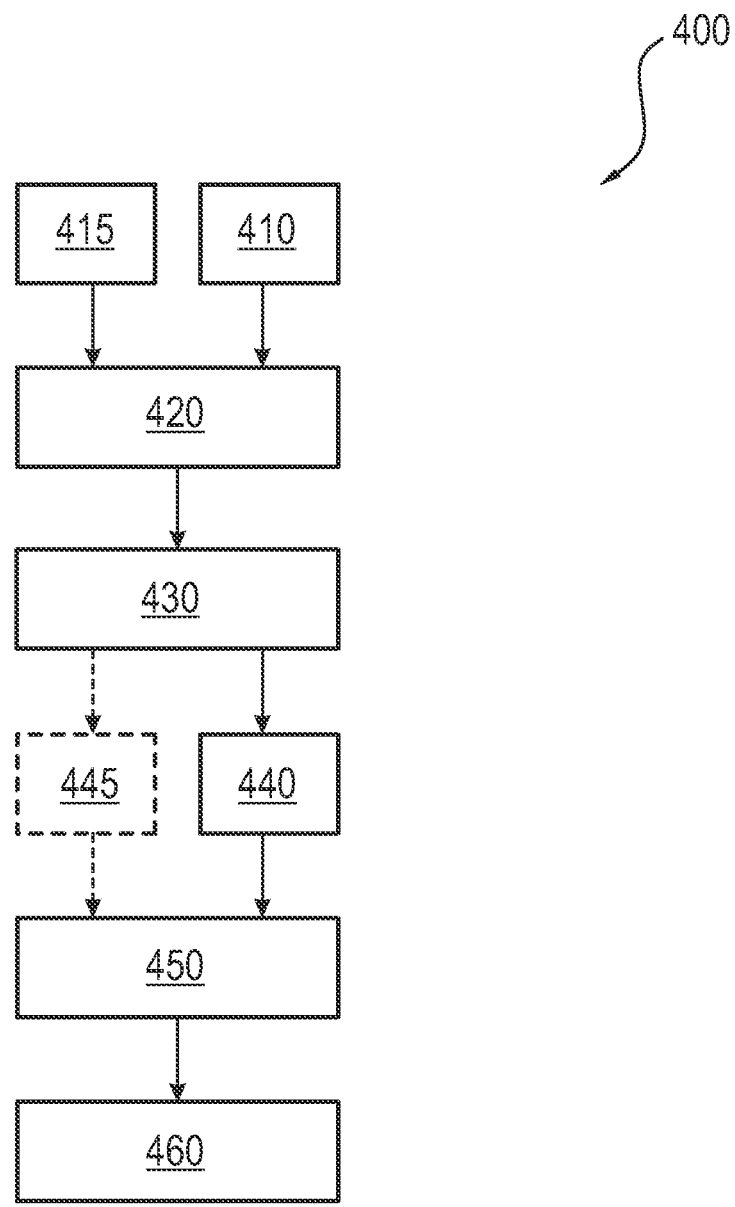
FIG. 4 is a flow chart of an exemplary embodiment of a process according to a third aspect of the present invention.

FIG. 4 shows a flow chart of an exemplary embodiment of a process 400 according to a third aspect of the present invention.

The process 400 according to the present invention is configured to regulate a gas flow within a ventilation system in the presence of an external gas flow source. The process 400 according to the present invention has the steps explained below.

A first step 410 comprises a reception of a first exhalation signal, which indicates a current expiratory gas flow. Another step 415, which is independent from the first step 410, comprises a reception of a first inhalation signal, which indicates a current inspiratory gas flow.

A next step 420 comprises a calculation of a leak flow on the basis of a difference between the current inspiratory gas flow and the current expiratory gas flow, while the external gas flow source is separated from a ventilation circuit of the ventilation system.

A next step 430 comprises an outputting of a leak signal, which indicates the determined leak flow.

A further step 440 comprises a reception of a second exhalation signal, which indicates a current aspiratory gas flow after the calculation of the leak flow.

A next step 450 comprises a calculation of an external gas flow after reception of the leak signal and after connection of the external gas flow source to the ventilation circuit of the ventilation system on the basis of the calculated leak flow and of the difference between the current inspiratory gas flow and the current expiratory gas flow.

A final step 460 comprises an outputting of an output signal, which is based on the calculated external gas flow.

Steps 410 and 415 may be carried out independently from one another and are preferably carried out at regular time intervals. Steps 420 and 430 are carried out in this order after steps 410, 415. The reception of the second inhalation signal in step 440 is preferably complemented by a reception of a second inhalation signal within the framework of step 445, which is drawn with broken lines. The two steps 440 and 445 are preferably carried out here independently from one another.

Steps 450 and 460 describe a second calculation maneuver, which follows chronologically the calculation maneuver according to steps 420 and 430.

The measurement of the external gas flow by the described calculation in the second calculation maneuver preferably needs to be carried out only once for a concrete external gas flow source, because the external gas flow does not typically change or shows hardly any change in case of the same external gas flow source.

A last step of the process according to the present invention preferably comprises a regulation of the inspiratory gas flow on the basis of the calculated external gas flow and/or on the basis of the calculated external gas flow and the calculated leak. The regulation is preferably based on a patient gas flow calculated within the process. A desirable patient gas flow is preferably predefined on the basis of a tidal volume of the ventilation, which tidal volume is set for the ventilation.

In an advantageous exemplary embodiment, the process according to the present invention makes possible a subsequent repeated calculation of the leak flow on the basis of the calculated external gas flow and of the difference between the current inspiratory gas flow and the current expiratory gas flow.

While specific embodiments of the invention have been shown and described in detail to illustrate the application of the principles of the invention, it will be understood that the invention may be embodied otherwise without departing from such principles.

LIST OF REFERENCE NUMBERS

100, 200, 300 Ventilation control unit
101 Housing
102 Gas flow
104 Patient
105, 205, 305 Ventilation system
106 Ventilation circuit
107, 307 Ventilator
108 Gas flow sensor
109 Y-piece
110, 310 External gas flow source
114 External gas port
116 Atomizer
120, 220, 320 Reception module
122, 222 Signal interface
125 Inspiratory flow signal
126 Inspiratory gas flow
127 Expiratory flow signal
128 Expiratory gas flow
130 First calculation module
132 Calculated leak flow
134 Leak signal
135 Second calculation module
136 Calculated external gas flow
140 Output module
142, 242, 342 Output signal
150 Actual leak flow
156 Actual external gas flow
223 First component of the signal interface
224 Second component of the signal interface
258 Actual patient gas flow
260 Additional calculation module
262 Calculated patient gas flow
270, 370 Regulating module
318 Control module
319 Opening device
380 First external interface
382 Second external interface
390 Leak calculation module
395 Processing unit
400 Process
410, 415, 420, 430, Process steps
440, 445, 450, 460

What is claimed is:

1. A ventilation control unit for regulating a gas flow within a ventilation system with a ventilation circuit and with an external gas flow source connected to the ventilation circuit, the ventilation control unit comprising:
   a reception module comprising a signal interface configured to repeatedly receive an inspiratory flow signal and an expiratory flow signal, wherein the inspiratory flow signal indicates a current inspiratory gas flow and the expiratory flow signal indicates a current expiratory gas flow;
   a first calculation module configured to calculate a leak flow based on a difference between the current inspiratory gas flow and the current expiratory gas flow, with the external gas flow source separated from the ventilation circuit of the ventilation system, and wherein the first calculation module is further configured to output a leak signal, which indicates the calculated leak flow, the calculated leak flow corresponding to a loss of fluid in the ventilation circuit;
   a second calculation module configured to receive the leak signal and to calculate an external gas flow with receipt of the leak signal, with a connection of the external gas flow source to the ventilation circuit of the ventilation system, based on the calculated leak flow and based on a difference between an updated current inspiratory gas flow and an updated current expiratory gas flow;

an output module configured to output an output signal, which is based on the calculated external gas flow; and a regulating module configured to receive the output signal and to trigger a regulation of an inspiratory gas flow based on the calculated external gas flow.

2. A ventilation control unit in accordance with claim 1, wherein the ventilation control unit is configured to be connected to the external gas flow source, the external gas flow source comprising an atomizer.

3. A ventilation control unit in accordance with claim 1, wherein the leak flow and/or the external gas flow are determined based on a plurality of inspiratory and expiratory gas flows of a corresponding plurality of breaths of a person connected to the ventilation system.

4. A ventilation control unit in accordance with claim 1, which is configured to calculate the leak flow based on the calculated external gas flow and based on the difference between the current inspiratory gas flow and the current expiratory gas flow.

5. A ventilation control unit in accordance with claim 1, further comprising an additional calculation module configured to calculate a patient gas flow fed to the patient based on the calculated external gas flow, based on the calculated leak flow and based on the difference between the current inspiratory gas flow and the current expiratory gas flow, wherein the output signal outputted by the output module indicates the patient gas flow.

6. A ventilation system comprising:
a ventilation circuit;
an external gas flow source; and
a ventilation control unit comprising:
  a reception module comprising a signal interface configured to repeatedly receive an inspiratory flow signal and an expiratory flow signal, wherein the inspiratory flow signal indicates a current inspiratory gas flow and the expiratory flow signal indicates a current expiratory gas flow;
  a first calculation module configured to calculate a leak flow based on a difference between the current inspiratory gas flow and the current expiratory gas flow, with the external gas flow source separated from the ventilation circuit, and wherein the first calculation module is further configured to output a leak signal, which indicates the calculated leak flow, the calculated leak flow corresponding to a loss of fluid in the ventilation circuit;
  a second calculation module configured to receive the leak signal and to calculate an external gas flow with receipt of the leak signal, with a connection of the external gas flow source to the ventilation circuit, based on the calculated leak flow and based on a difference between an updated current inspiratory gas flow and an updated current expiratory gas flow; and
  an output module configured to output an output signal, which is based on the calculated external gas flow.

7. A ventilation system in accordance with claim 6, further comprising a control module for control of the external gas flow source, wherein the control module is configured to maintain the external gas flow source separated from the ventilation circuit prior to the reception of the leak signal provided by the first calculation module and to trigger a connection of the external gas flow source to the ventilation circuit with a reception of the leak signal.

8. A ventilation system in accordance with claim 6, wherein the ventilation control unit further comprises a regulating module configured to receive the output signal and to trigger a regulation of an inspiratory gas flow based on the calculated external gas flow.

9. A ventilation system in accordance with claim 6, wherein the external gas flow source comprises an atomizer.

10. A ventilation system in accordance with claim 6, wherein the leak flow and/or the external gas flow are determined based on a plurality of inspiratory and expiratory gas flows of a corresponding plurality of breaths of a person connected to the ventilation system.

11. A ventilation system in accordance with claim 6, which is configured to calculate the leak flow based on the calculated external gas flow and based on the difference between the current inspiratory gas flow and the current expiratory gas flow.

12. A ventilation system in accordance with claim 6, wherein the ventilation control unit further comprises an additional calculation module configured to calculate a patient gas flow fed to the patient based on the calculated external gas flow, based on the calculated leak flow and based on the difference between the current inspiratory gas flow and the current expiratory gas flow, wherein the output signal outputted by the output module indicates the patient gas flow.

13. A process for regulating a gas flow within a ventilation system with a ventilation circuit with an external gas flow source, the process comprising the steps of:
receiving a first inhalation signal, which indicates a current inspiratory gas flow, and receiving a first exhalation signal, which indicates a current expiratory gas flow;
calculating a leak flow based on a difference between the current inspiratory gas flow and the current expiratory gas flow with the external gas flow source separated from the ventilation circuit of the ventilation system;
outputting a leak signal, which indicates the determined leak flow;
receiving a second exhalation signal, which indicates a current expiratory gas flow after the calculation of the leak flow;
calculating an external gas flow after receiving the leak signal, with a connection of the external gas flow source to the ventilation circuit of the ventilation system, based on the calculated leak flow and based on the difference between an updated current inspiratory gas flow and an updated current expiratory gas flow, the calculated leak flow corresponding to a loss of fluid in the ventilation circuit; and
outputting an output signal, which is based on the calculated external gas flow.

14. A process in accordance with claim 13, wherein the step of outputting an output signal comprises a regulation of an inspiratory gas flow based on the calculated external gas flow.

15. A process in accordance with claim 14, wherein the inspiratory gas flow is regulated, furthermore, based on the calculated leak flow.

16. A process in accordance with claim 13, further comprising a reception of a second inhalation signal, which indicates a current inspiratory gas flow, after the calculation of the leak flow.

17. A process in accordance with claim 13, further comprising a repeated calculation of the leak flow based on the calculated external gas flow and based on the difference between the current inspiratory gas flow and the current expiratory gas flow.

18. A process in accordance with claim 13, wherein a regulating module is provided and configured to receive the output signal and to trigger a regulation of an inspiratory gas flow based on the calculated external gas flow.

19. A process in accordance with claim 13, wherein a control module is provided for control of the external gas flow source, wherein the control module is configured to maintain the external gas flow source separated from the ventilation circuit prior to the reception of the leak signal provided by the first calculation module and to trigger a connection of the external gas flow source to the ventilation circuit with a reception of the leak signal.

* * * * *